(12) United States Patent
Jeffrey et al.

(10) Patent No.: US 6,805,120 B1
(45) Date of Patent: Oct. 19, 2004

(54) BREATHING ASSISTANCE APPARATUS

(75) Inventors: Craig Robert Jeffrey, Auckland (NZ); Graeme Woolmore, Auckland (NZ); Anthony James Newland, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 564 days.

(21) Appl. No.: 09/658,551

(22) Filed: Sep. 8, 2000

(30) Foreign Application Priority Data

Sep. 20, 1999 (NZ) .................................. 337950

(51) Int. Cl.[7] ........................................... A61M 16/00
(52) U.S. Cl. ........................... 128/204.23; 128/204.22; 128/204.18; 128/204.17
(58) Field of Search ................ 128/204.14, 204.17, 128/205.24, 204.23, 203.26, 203.27, 203.29, 911, 913, 203.16, 203.17, 200.14, 204.18, 204.22; 137/251.1, 123, 145, 150.5, 152

(56) References Cited

U.S. PATENT DOCUMENTS

| | | | |
|---|---|---|---|
| 2,918,917 A | 12/1959 | Emerson | |
| 2,989,069 A * | 6/1961 | Nixon | 137/251.1 |
| 3,912,795 A * | 10/1975 | Jackson | 261/36.1 |
| 3,923,057 A * | 12/1975 | Chalon | 128/203.16 |
| 3,972,326 A | 8/1976 | Brawn | 128/202.18 |
| 3,990,441 A * | 11/1976 | Hoyt et al. | 128/200.18 |
| 4,010,748 A * | 3/1977 | Dobritz | 128/203.27 |
| 4,011,866 A * | 3/1977 | Klein et al. | 128/204.21 |
| 4,185,414 A * | 1/1980 | Miller | 47/62 C |
| 4,232,667 A * | 11/1980 | Chalon et al. | 128/203.26 |
| 4,265,237 A | 5/1981 | Schwanbom et al. | |
| 4,459,983 A | 7/1984 | Beyreuther et al. | 128/205.24 |
| 4,597,917 A * | 7/1986 | Lunsford | 261/153 |
| 4,646,733 A | 3/1987 | Stroh et al. | |
| 4,821,709 A | 4/1989 | Jensen | |
| 4,829,998 A * | 5/1989 | Jackson | 128/203.12 |
| 5,195,515 A * | 3/1993 | Levine | 128/203.26 |
| 5,988,164 A * | 11/1999 | Paluch | 128/203.26 |
| 6,041,777 A * | 3/2000 | Faithfull et al. | 128/200.24 |

FOREIGN PATENT DOCUMENTS

| | | |
|---|---|---|
| EP | 513712 | 11/1992 |
| FR | 2222074 | 10/1974 |

* cited by examiner

*Primary Examiner*—Henry Bennett
*Assistant Examiner*—Mital Patel
(74) *Attorney, Agent, or Firm*—Trexler, Bushnell, Giangiorgi, Blackstone & Marr, Ltd.

(57) ABSTRACT

A pressure regulator for regulating the expiratory flow in a CPAP system includes submerging a tube into a column of water. Improvements are included for adjusting the level to which the tube is submerged and for ensuring constant water level.

9 Claims, 4 Drawing Sheets

BREATHING ASSISTANCE APPARATUS

BACKGROUND TO THE INVENTION i) Field of the Invention

The present invention relates to the use of a pressure regulator in conjunction with a breathing assistance apparatus, particularly though not solely, for regulating the pressure of gases supplied to a patient from a humidified Positive End Expiratory Pressure (PEEP) apparatus.

ii) Summary of the Prior Art

The use of a medical apparatus to facilitate breathing is well known in the art. The apparatus may take the form of a simple oxygen mask or tent which supplies oxygen at slightly above atmospheric pressure. Such devices merely assist a person to breath and work with the person's lungs.

Ventilators which operate at high frequency have been suggested in the past. There are two types of high frequency ventilators known in the art. One type, as exemplified by U.S. Pat. No. 2,918,917 (Emerson), employs a reciprocating diaphragm to vibrate a column of gas supplied to a subject. The vibration is in addition to the subject's respiration, natural or artificial, and at a much more rapid rate, for example, from 100 to more than 1500 vibrations per minute. The Emerson apparatus is primarily designed to vibrate the patient's airway and organs associated therewith, although Emerson also recognized that high frequency vibration causes the gas to diffuse more rapidly within the airway and therefore aids the breathing function. However, the Emerson is incapable of supporting the patient's full ventilation and must be used in conjunction with the patient's spontaneous breathing or with another apparatus which produces artificially induced inhalation and exhalation.

The second type of high frequency ventilator is the jet pulse ventilator as exemplified in U.S. Pat. No. 4,265,237 (Schwanbom et al.). The Schwanbom et al. ventilator produces high frequency, high pressure pulses of air which are capable of fully ventilating a patient. The respiration pulse enters with a pressure of 0.2 bar to 2.7 bar. This pressure is sufficient to expand the lungs during inspiration. Expiration is caused by the natural compliance of the lungs after the jet of air is stopped. Accordingly, it can be see that Schwanbom et al must rely on the compliance of the lungs in order to fully ventilate the patient. If the lung compliance is low, greater pressure must be used. Schwanbom et al also supply a source of lower pressure gas for spontaneous breathing by the patient. While such jet pulse ventilators are useful for some applications, they are not generally applicable and their use is limited mostly to experimental work.

An improvement on these types is disclosed in U.S. Pat. No. 4,821,709 (Jensen) a which provides high frequency oscillations in the gases supplied to a patient using a flexible diaphragm. Jensen provides a more practical method of ventilating a patient without spontaneous breathing of the patient, or the need for a separate ventilator. U.S. Pat. No. 4,646,733 (Strot et al.) proposes an apparatus for producing high frequency oscillations in gases supplied to a patient using a valve controlling the exhaled gases.

It would be desirable to have a simple system for providing high frequency pressure oscillations for spontaneously breathing patients particularly for non invasive forms of support, where the means level of gases provided to the patient can be adjusted.

SUMMARY OF THE INVENTION

It is an object of the present invention to provide a pressure regulator which goes some way to overcoming the above-mentioned disadvantages, or which will at least provide the healthcare industry with a useful choice.

Accordingly, in a first aspect, the present invention consists in a pressure regulating device for use with a breathing assistance apparatus which conveys inhalatory gas to, and removes exhalatory gas from a patient requiring breathing assistance, comprising:

a container which in use includes a body of liquid, having a substantially constant level in use, a terminal conduit including proximate and distal ends, said proximate end adapted for connection to a breathing assistance apparatus and in use accepting exhalatory gas therefrom, and said distal end submerged in said body of liquid, such that in use the mean pressure of said gas supplied to a patient is adjusted by the level to which said distal end is submerged in said body of liquid.

In a second aspect, the present invention consists in a breathing assistance apparatus for supplying gas to a patient to assist said patient's breathing a gas supply adapted to supply gas to said patient, an interface including a plurality of ports adapted to deliver said gas to said patient, an inhalatory conduit for conveying said gas from said gas supply to said interface, exhalatory conduit for conveying said patient's exhalations from said interface a container which in use includes a body of liquid, and a terminal conduit including proximate and distal ends, said proximate end adapted for connection to said exhalatory conduit and in use accepting exhalatory gas therefrom, and said distal end submerged in said body of liquid, such that in use said patient is delivered a substantially constant mean pressure, said mean pressure adjusted by the level to which said distal end is submerged in said body of water.

In a third aspect, the present invention consists in a pressure regulating device for use with a breathing assistance apparatus which conveys inhalatory gas to, and removes exhalatory gas from a patient requiring breathing assistance, comprising:

a container which in use includes a body of liquid having substantially constant level in use, and a terminal conduit including proximate and distal ends, said proximate end adapted for connection to a breathing assistance apparatus and accepting exhalatory gas therefrom, and said distal end submerged in said body of liquid, such that in use the resultant bubbling occurring in said body of liquid produces relatively small controlled perturbations in the pressure of gas supplied to a patient.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION OF THE PREFERRED EMBODIMENTS

The present invention provides a means of producing the variations or oscillations in the pressure of gases supplied to a patient connected to a positive pressure ventilation device. By submerging the end of the exhalatory conduit into a water column the resulting bubbles generate a variation or ripple in the mean pressure of gases delivered to the patient. In doing so it also provides a simple method of varying the mean pressure of gases supplied to the patient by variation of the level to which the end of the exhalatory conduit is submerged within the water column. In order to keep the mean pressure of gases supplied to the patient constant the level of submergence of the end of the exhalatory conduit must be kept constant and an apparatus for ensuring this occurs is also disclosed.

Figure 1:
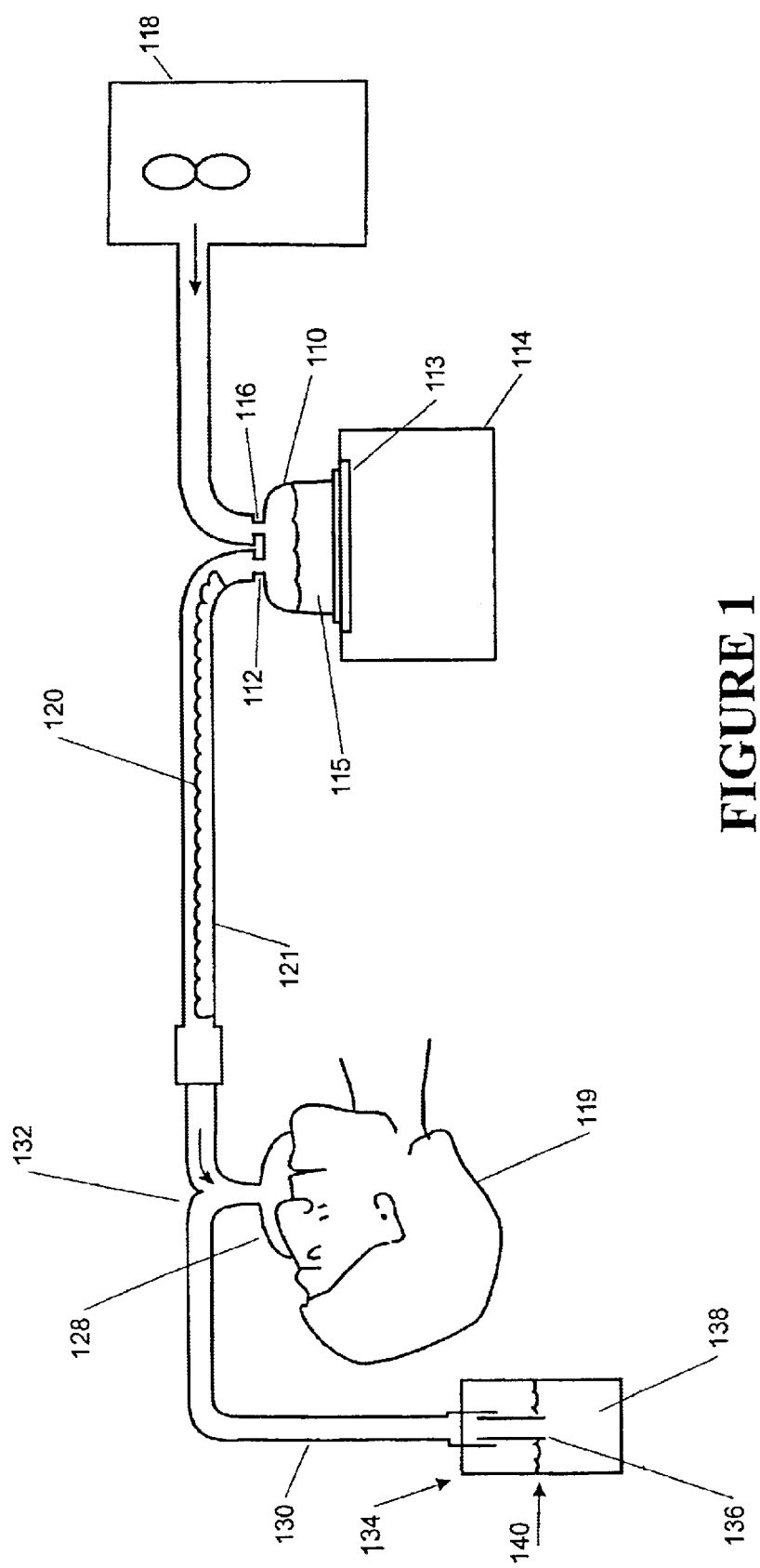
FIG. 1 is a block diagram showing a typical configuration for supplying breathing assistance to a patient.
Figure 5:
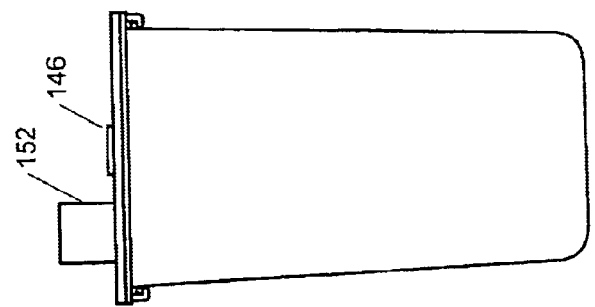
FIG. 5 is an alternative side view of the pressure regulator according to the preferred embodiment of the present invention.

Referring now to FIG. 1 in which a typical application is depicted. A humidified Positive End Expiratory Pressure (PEEP) system is shown in which a patient 119 is receiving humidified 114 and pressurised gas through a nasal mask 128 connected to an inhalatory conduit 121. It should be understood that the present invention, however, is not limited to the delivery of PEEP gases but is also applicable to other types of gases delivery systems and may not necessarily involve humidification. Inhalatory conduit 121 is connected to the outlet 112 of a humidification chamber 110 which contains a volume of water 115. Inspiratory conduit 121 may contain heating means or heater wires 120 which heat the walls of the conduit to ensure a constant humidity profile along the conduit and therefore reduce condensation of humidified gases within the conduit. As the volume of water 115 within humidification chamber 110 is heated 113, water vapour begins to fill the volume of the chamber above the water's surface and is passed out of the humidification chamber 110 outlet 112 with the flow of gases (for example air) provided from a gases supply means or blower 118 which enters the chamber 110 through inlet 116.

The humidified gases pass through the inhalatory conduit 121 to the mask 128 attached around the patient's 119 mouth. The excess gases then flow through the exhalatory conduit 130 to a pressure regulator 134.

Pressure Regulator

In the preferred embodiment of the present invention the pressure regulator 134, takes the form of discharging the flow of exhalatory gases into a chamber 204 containing a column of water 138. The gases flowing through the exhalatory conduit 130 are discharged into the body of water 138 from short conduit 136 which extends from the expiratory conduit into the chamber 204. This results in a bubbling effect, whereby the gases eventually exit the chamber 204 via the outlet port 152, which can also be used to initially fill the chamber 204 with water. The outlet port 152 includes shielding to prevents liquid aerosols created by the vigorous bubbling on the surface of the water from being expelled. It will be appreciated that the short conduit 136, could equally be integrated into the end of the expiratory conduit 130.

Figure 2:
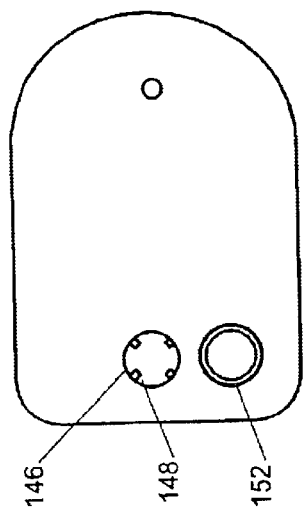
FIG. 2 is a plan view of the pressure regulator with the lid on according to the preferred embodiment of the present invention.
Figure 4:
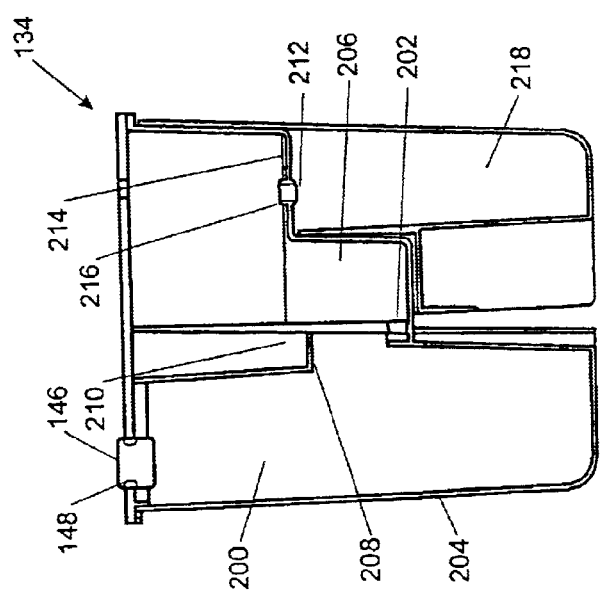
FIG. 4 is a cross-section of the pressure regulator according to the preferred embodiment of the present invention.
Figure 3:
FIG. 3 is a side view of the pressure regulator according to the preferred embodiment of the present invention.
Figure 6:
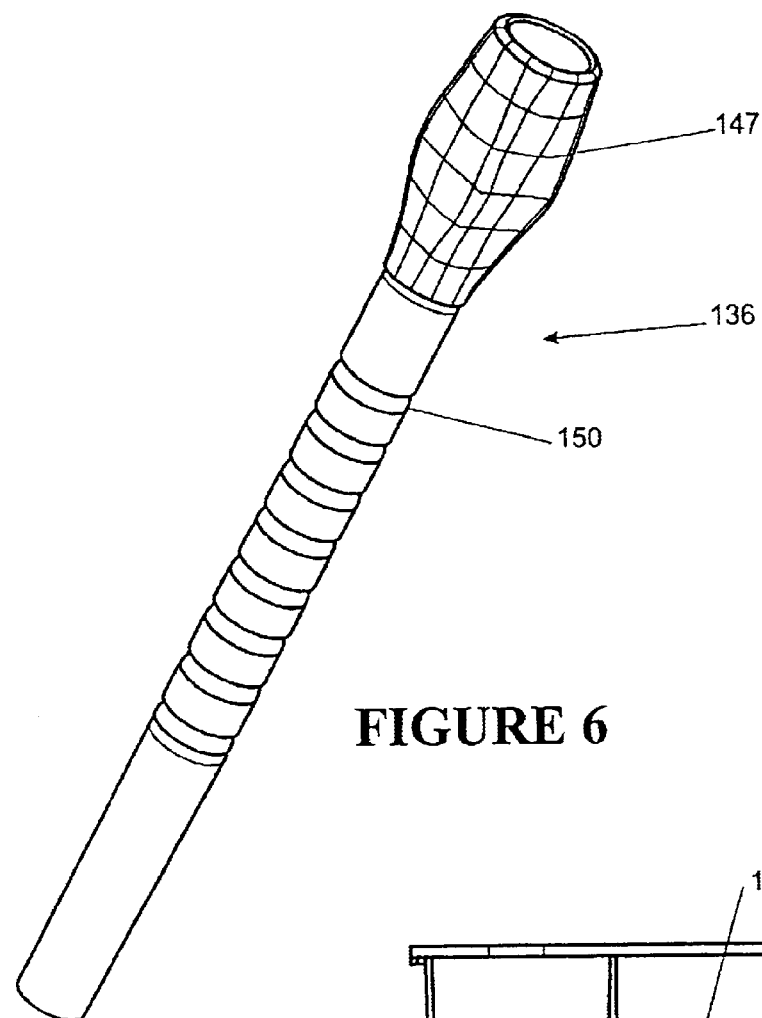
FIG. 6 is a perspective view of the short conduit which extends into the water chamber according to the preferred embodiment of the present invention.

Referring now to FIGS. 2 through to 7, the pressure regulator 134 and associated components are seen in more detail. The exhalatory conduit (130, FIG. 1) fits into the end of the short conduit 136 which in turn is attached to the lid 144 of the water chamber 204 via connector 146. The connector 146 includes a number of resilient ridges or plastic toggles 148 which lock into annular grooves 150 in the short conduit 136 to keep it locked in a desired position during use. The chamber 204 is filled with a body of water 138 up to a predetermined level 140. It will be appreciated that any appropriate liquid could be used instead of water.

Figure 7:
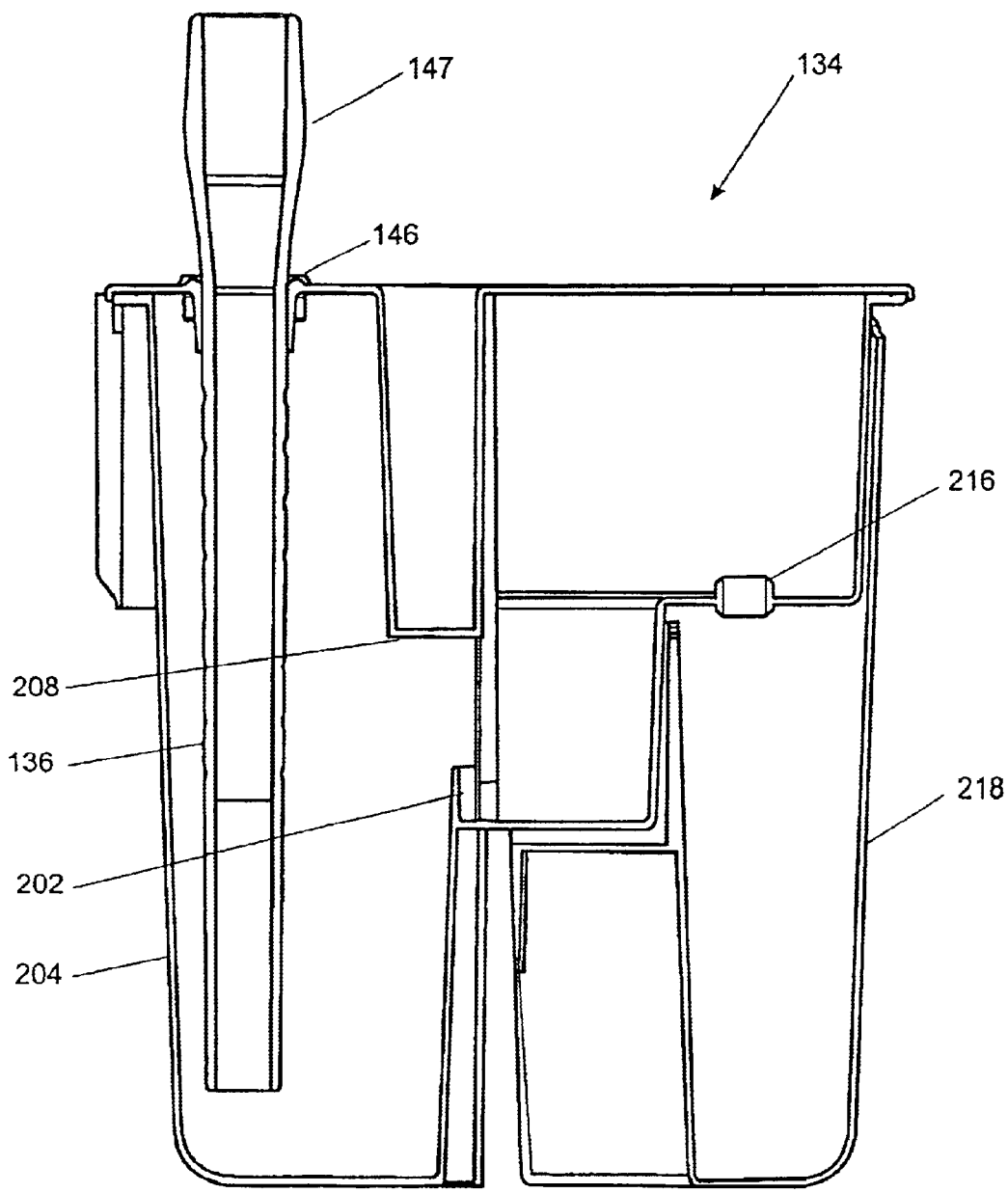
FIG. 7 is a cross-section of the complete pressure regulator according to the preferred embodiment of the present invention.

It will be appreciated that for control over the mean pressure of supplied gases it is necessary to vary the level of which the short conduit 136 is submerged in the body of water 138. Stepped variations in the pressure of gases delivered to the patient of ½ cm H₂O each, are thought adequate for most applications, and is achieved by spacing each of the annular grooves 150½ cm apart. A contoured gripping portion 147 is provided at the end of the short conduit 136 which attaches to the exhalatory conduit 130, to allow easy adjustment. In one embodiment, the pressure is adjustable over a range from 4–8 cm H₂O but it will be appreciated that this can be modified to requirements. The pressure regulator according to the preferred embodiment of the present invention is shown in FIG. 7, adjusted to its highest pressure setting. The settings could be indicated by a number above each groove 150 on the short conduit 136, which would be visible above the connector 146.

Constant Water Level

In the preferred embodiment, the present invention is used in conjunction with a humidified PEEP respirator. As such, the exhalatory gases will have quite high levels of humidity, some at which will inevitably condense in the body of water 138 in the pressure regulator 134. Thus, over time the volume of water in the water chamber 204 will rise and if unchecked will result in rising pressure of gases supplied to the patient and resultant adverse side effects. To ensure the water level is kept constant the water chamber 204 is provided with an overflow facility 218 also seen in FIGS. 2 to 7.

Because of the vigorous bubbling occurring at the top of the body of water a simple lip over which excess liquid can flow would be ineffective and therefore some form of filtering or damping is required. In order to mitigate the effect of the vigorous bubbling near the top of the chamber 200 a main outlet port 202 from the main chamber 204 is provided at a substantially lower level than where the bubbles would normally be expected to occur. However, the bubbling also causes pressure waves throughout the body of the liquid. These pressure waves would normally be reflected through the main outlet port 202 into the levelling chamber 206 and therefore result in more water escaping than it is desired. To alleviate the effect of the pressure waves a wave shield 208 is located in an intermediate position between the upper level of the water 210 and the main outlet port 202. This masks the outlet port 202 from the majority of the pressure waves due to the surface bubbling.

This effectively means that the water level in the levelling chamber 206 is relatively calm and substantially representative of the mean (as opposed to the instantaneous) water level in the main chamber 204. The water level in the intermediate overflow chamber 206 in turn is regulated by an overflow port 212 situated on a raised adjacent platform 214. The overflow port 212 is surrounded by a slightly cylindrical raised partition 216 in order to overcome the effect of any small remaining waves in the intermediate overflow chamber 206.

The water then flows into the detachable overflow container 218 which when full may be detached in use and emptied. Both the main chamber 204 and the intermediate overflow chamber 206 are integrally injection moulded using a clear plastic. The separate overflow container 218, is also injection moulded using a clear plastic as is the separate short conduit 136.

Further Embodiments

Figure 8:
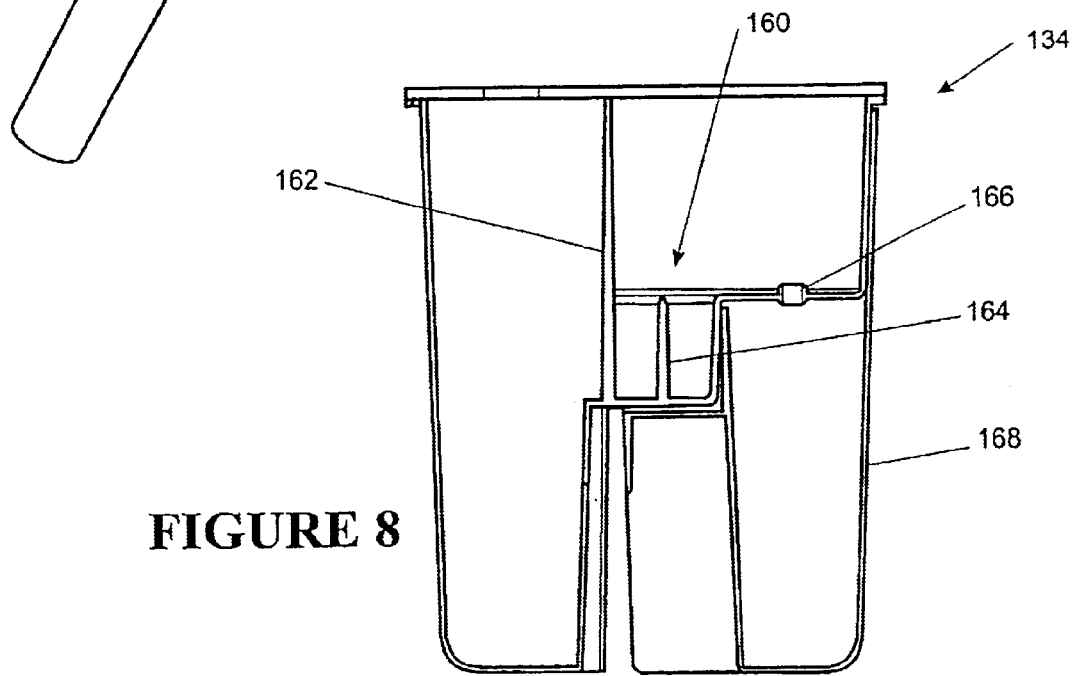
FIG. 8 is a cross-section of a further embodiment of the present invention.

It will also be appreciated that the apparatus used to vary the mean water level in the main chamber may take a number of forms. While in the preferred embodiment a slidable conduit is used, other forms such a concertina baffle or rotatable conduit, for example, would be equally applicable. It will also be appreciated further forms of the overflow facility will be possible. For example the further embodiment shown in FIG. 8, uses a thin slot 162 to pass water into a second chamber 160, where baffles 164 smooth any variations before the overflow opening 166 into the overflow chamber 168.

Advantages

Allows easy adjustment of the mean pressure level.

Allows high frequency pressure oscillations for spontaneously breathing patients.

Maintains constant mean pressure with low or no maintenance.

Disposable and cheap compared with prior art ventilators.

What is claimed is:

1. A pressure regulating device for use with a breathing assistance apparatus which conveys inhalatory gas to, and removes exhalatory gas from a patient requiring breathing assistance, comprising:

a container which in use includes a body of liquid, configured to have a substantially constant level in use, and an overflow outlet adjacent said constant level, a terminal conduit including proximate and distal ends, said proximate end adapted for connection to a breathing assistance apparatus and in use accepting exhalatory gas therefrom, and said distal end submerged in said body of liquid, such that in use the mean pressure of said gas supplied to a patient is adjusted by the level to which said distal end is submerged in said body of water.

2. A pressure regulating device as claimed in claim 1, further comprising a connector attached to said container and engaging said terminal conduit, whereby in use said terminal conduit may be adjusted in axial position in predetermined increments, with respect to said connector.

3. A pressure regulating device as claimed in claim 2 wherein said terminal conduit includes at least one partial groove and said connector includes at least one matching partial resilient ridge or toggle.

4. A pressure regulating device as claimed in either of claim 2 or 3 wherein said predetermined increments are one centimeter each.

5. A pressure regulating device as claimed in claim 1 wherein said overflow outlet also includes damping means associated with said outlet.

6. A pressure regulating device as claimed in claim 5 wherein said damping means comprises an underwater outlet from said container which is located at a position which in use is substantially below the level of said body of liquid, and a wave shield located at a position which in use is between the level of said body of liquid and said underwater outlet.

7. A pressure regulating device as claimed in claim 1 further comprising a removable container, whereby in use the overflow from said body of liquid flows through said overflow outlet into said removable container.

8. A pressure regulating device as claimed in claim 7 wherein said body of liquid is substantially composed of water.

9. A pressure regulating device as claimed in claim 8 wherein said device is constructed substantially from clear plastic materials.

* * * * *

UNITED STATES PATENT AND TRADEMARK OFFICE
CERTIFICATE OF CORRECTION

PATENT NO. : 6,805,120 B1
DATED : October 19, 2004
INVENTOR(S) : Craig Robert Jeffrey, Graeme Woolmore and Anthony James Newland It is certified that error appears in the above-identified patent and that said Letters Patent is hereby corrected as shown below:

Column 6,
Line 19, "claim" should be -- claims --

Signed and Sealed this

Fifteenth Day of February, 2005

JON W. DUDAS
*Director of the United States Patent and Trademark Office*